(12) United States Patent
Savage et al.

(10) Patent No.: US 8,252,047 B2
(45) Date of Patent: Aug. 28, 2012

(54) DRUG-DELIVERY ENDOVASCULAR STENT AND METHOD FOR TREATING RESTENOSIS

(75) Inventors: Douglas R. Savage, Del Mar, CA (US); Ronald E. Betts, La Jolla, CA (US)

(73) Assignee: Biosensors International Group, Ltd., Hamilton (BM)

( * ) Notice: Subject to any disclaimer, the term of this patent is extended or adjusted under 35 U.S.C. 154(b) by 0 days.

(21) Appl. No.: 13/023,312

(22) Filed: Feb. 8, 2011

(65) Prior Publication Data

US 2011/0123704 A1    May 26, 2011

Related U.S. Application Data

(62) Division of application No. 11/232,598, filed on Sep. 22, 2005, now Pat. No. 7,901,451.

(60) Provisional application No. 60/613,071, filed on Sep. 24, 2004.

(51) Int. Cl.
*A61F 2/82*    (2006.01)

(52) U.S. Cl. ....... 623/1.42; 623/1.46; 623/903; 424/423

(58) Field of Classification Search ........ 623/1.42–1.46; 424/422–425; 427/2.25
See application file for complete search history.

(56) References Cited

U.S. PATENT DOCUMENTS

| | | | |
|---|---|---|---|
| 3,929,992 A | 12/1975 | Sehgal et al. | |
| 4,316,885 A | 2/1982 | Rakhit | |
| 4,374,669 A | 2/1983 | MacGregor | |
| 4,650,803 A | 3/1987 | Stella et al. | |
| 4,885,171 A | 12/1989 | Surendra et al. | |
| 4,990,155 A | 2/1991 | Wilkoff | |
| 5,100,899 A | 3/1992 | Calne | |
| 5,120,842 A | 6/1992 | Failli et al. | |
| 5,151,413 A | 9/1992 | Caufield et al. | |
| 5,163,952 A | 11/1992 | Froix | |

(Continued)

FOREIGN PATENT DOCUMENTS

EP    0875218    11/1998

(Continued)

OTHER PUBLICATIONS

Farb et al., "Extracellular Matrix Changes in Stented Human Coronary Arteries," Circulation vol. 110, No. 8, 2004, pp. 940-947.

(Continued)

*Primary Examiner* — Brian Pellegrino
*Assistant Examiner* — Megan Wolf
(74) *Attorney, Agent, or Firm* — Kilpatrick Townsend & Stockton LLP (57) ABSTRACT

A radially expandable, endovascular stent designed for placement at a site of vascular injury, for inhibiting restenosis at the site, a method of using, and a method of making the stent. The stent includes a radially expandable body formed of one or more metallic filaments and a liquid-infusible mechanical anchoring layer attached to or formed in outer surface of the filaments. A drug coating in the stent is composed of a substantially polymer-free composition of an anti-restenosis drug, and has a substratum infused in the anchoring layer and a substantially continuous surface stratum of drug that is brought into direct contact with the vessel walls at the vascular site. Thus, the rate of release of the anti-restenosis drug from the surface stratum into said vascular site is determined solely by the composition of said drug coating.

6 Claims, 4 Drawing Sheets

U.S. PATENT DOCUMENTS

| | | |
|---|---|---|
| 5,258,020 A | 11/1993 | Froix |
| 5,258,389 A | 11/1993 | Goulet et al. |
| 5,288,711 A | 2/1994 | Mitchell et al. |
| 5,306,286 A | 4/1994 | Stack et al. |
| 5,342,348 A | 8/1994 | Kaplan |
| 5,362,718 A | 11/1994 | Skotnicki et al. |
| 5,441,515 A | 8/1995 | Khosravi et al. |
| 5,464,650 A | 11/1995 | Berg et al. |
| 5,516,781 A | 5/1996 | Morris et al. |
| 5,527,337 A | 6/1996 | Stack et al. |
| 5,607,467 A | 3/1997 | Froix |
| 5,609,629 A | 3/1997 | Fearnot et al. |
| 5,649,977 A | 7/1997 | Campbell |
| 5,665,772 A | 9/1997 | Cottens et al. |
| 5,707,385 A | 1/1998 | Williams |
| 5,713,949 A | 2/1998 | Jayaraman |
| 5,716,981 A | 2/1998 | Hunter et al. |
| 5,733,327 A | 3/1998 | Igaki et al. |
| 5,769,884 A | 6/1998 | Solovay |
| 5,824,048 A | 10/1998 | Tuch |
| 5,843,172 A | 12/1998 | Van |
| 5,860,999 A | 1/1999 | Schnepp-Pesch et al. |
| 5,873,904 A | 2/1999 | Ragheb et al. |
| 5,895,407 A | 4/1999 | Jayaraman |
| 5,902,317 A | 5/1999 | Kleshinski et al. |
| 5,912,253 A | 6/1999 | Cottens et al. |
| 5,922,393 A | 7/1999 | Jayaraman |
| 5,972,027 A | 10/1999 | Johnson |
| 6,013,853 A | 1/2000 | Athanasiou et al. |
| 6,019,784 A | 2/2000 | Hines |
| 6,022,371 A | 2/2000 | Killion |
| 6,042,606 A | 3/2000 | Frantzen |
| 6,071,305 A | 6/2000 | Brown et al. |
| 6,080,177 A | 6/2000 | Igaki et al. |
| 6,096,175 A | 8/2000 | Roth |
| 6,099,561 A | 8/2000 | Alt |
| 6,099,562 A | 8/2000 | Ding et al. |
| 6,129,755 A | 10/2000 | Mathis et al. |
| 6,153,252 A | 11/2000 | Hossainy et al. |
| 6,156,062 A | 12/2000 | McGuinness |
| 6,159,488 A | 12/2000 | Nagler |
| 6,171,609 B1 | 1/2001 | Kunz |
| 6,174,329 B1 | 1/2001 | Callol et al. |
| 6,190,406 B1 | 2/2001 | Duerig et al. |
| 6,197,013 B1 | 3/2001 | Reed et al. |
| 6,203,536 B1 | 3/2001 | Berg et al. |
| 6,231,600 B1 | 5/2001 | Zhong |
| 6,240,616 B1 | 6/2001 | Van |
| 6,248,129 B1 | 6/2001 | Froix |
| 6,258,121 B1 | 7/2001 | Yang et al. |
| 6,273,913 B1 | 8/2001 | Wright et al. |
| 6,274,294 B1 | 8/2001 | Hines |
| 6,299,604 B1 | 10/2001 | Ragheb et al. |
| 6,368,346 B1 | 4/2002 | Jadhav |
| 6,368,658 B1 | 4/2002 | Schwarz et al. |
| 6,379,381 B1 | 4/2002 | Hossainy et al. |
| 6,384,046 B1 | 5/2002 | Schuler et al. |
| 6,527,919 B1 | 3/2003 | Roth |
| 6,540,777 B2 | 4/2003 | Stenzel |
| 6,544,582 B1 | 4/2003 | Yoe |
| 6,585,151 B1 | 7/2003 | Ghosh |
| 6,585,764 B2 | 7/2003 | Wright et al. |
| 6,607,598 B2 | 8/2003 | Schwarz et al. |
| 6,623,521 B2 | 9/2003 | Steinke et al. |
| 6,641,611 B2 | 11/2003 | Jayaraman |
| 6,652,581 B1 | 11/2003 | Ding |
| 6,663,881 B2 | 12/2003 | Kunz et al. |
| 6,670,398 B2 | 12/2003 | Edwards et al. |
| 6,676,701 B2 | 1/2004 | Rourke et al. |
| 6,709,379 B1 | 3/2004 | Brandau et al. |
| 6,730,064 B2 | 5/2004 | Rajheb et al. |
| 6,730,120 B2 | 5/2004 | Berg et al. |
| 6,739,831 B2 | 5/2004 | Hsu et al. |
| 6,743,463 B2 | 6/2004 | Weber et al. |
| 6,746,773 B2 | 6/2004 | Llanos et al. |
| 6,774,278 B1 | 8/2004 | Rajheb et al. |
| 6,790,228 B2 | 9/2004 | Hossainy et al. |
| 6,805,898 B1 | 10/2004 | Wu et al. |
| 6,904,658 B2 | 6/2005 | Hines |
| 6,911,100 B1 | 6/2005 | Gibbs et al. |
| 6,913,617 B1 | 7/2005 | Reiss |
| 6,919,100 B2 | 7/2005 | Narayanan |
| 6,939,376 B2 | 9/2005 | Shulze et al. |
| 7,055,237 B2 | 6/2006 | Thomas |
| 7,128,755 B2 | 10/2006 | Su et al. |
| 2001/0002935 A1 | 6/2001 | Greenberg et al. |
| 2001/0020151 A1 | 9/2001 | Reed et al. |
| 2001/0027340 A1 | 10/2001 | Wright et al. |
| 2001/0029351 A1 | 10/2001 | Falotico et al. |
| 2002/0005600 A1 | 1/2002 | Ma |
| 2002/0038146 A1 | 3/2002 | Ulf |
| 2002/0051730 A1 | 5/2002 | Bodnar et al. |
| 2002/0082679 A1 | 6/2002 | Sirhan et al. |
| 2002/0098278 A1 | 7/2002 | Bates et al. |
| 2002/0111590 A1 | 8/2002 | Davila et al. |
| 2002/0111671 A1 | 8/2002 | Stenzel |
| 2002/0156022 A1 | 10/2002 | Edwards et al. |
| 2003/0033007 A1 | 2/2003 | Sirhan et al. |
| 2003/0050687 A1 | 3/2003 | Schwade et al. |
| 2003/0050692 A1 | 3/2003 | Sirhan et al. |
| 2003/0059454 A1 | 3/2003 | Barry et al. |
| 2003/0068355 A1 | 4/2003 | Shanley et al. |
| 2003/0077310 A1 | 4/2003 | Pathak et al. |
| 2003/0083646 A1 | 5/2003 | Sirhan et al. |
| 2003/0139801 A1 | 7/2003 | Sirhan et al. |
| 2003/0159920 A1 | 8/2003 | Roth |
| 2003/0176915 A1 | 9/2003 | Wright et al. |
| 2003/0225450 A1 | 12/2003 | Shulze et al. |
| 2004/0010002 A1 | 1/2004 | Wasik et al. |
| 2004/0024450 A1 | 2/2004 | Shulze et al. |
| 2004/0030380 A1 | 2/2004 | Shulze et al. |
| 2004/0073284 A1 | 4/2004 | Bates et al. |
| 2004/0109937 A1 | 6/2004 | Jennissen et al. |
| 2004/0249442 A1 | 12/2004 | Fleming et al. |
| 2005/0038505 A1 | 2/2005 | Shulze et al. |
| 2005/0101624 A1 | 5/2005 | Betts et al. |
| 2005/0271701 A1 | 12/2005 | Cottone et al. |
| 2006/0002968 A1 | 1/2006 | Stewart et al. |
| 2006/0036316 A1 | 2/2006 | Zeltinger et al. |
| 2006/0069427 A1 | 3/2006 | Savage et al. |
| 2006/0155361 A1 | 7/2006 | Schomig et al. |
| 2006/0229711 A1 | 10/2006 | Yan et al. |
| 2008/0051868 A1 | 2/2008 | Cottone et al. |
| 2008/0051873 A1 | 2/2008 | Cottone et al. |
| 2008/0051874 A1 | 2/2008 | Cottone et al. |
| 2008/0051875 A1 | 2/2008 | Cottone et al. |
| 2008/0097575 A1 | 4/2008 | Cottone |

FOREIGN PATENT DOCUMENTS

| | | |
|---|---|---|
| EP | 0950386 | 10/1999 |
| EP | 0970711 | 1/2000 |
| JP | 10192413 | 7/1998 |
| WO | WO 97/35575 | 10/1997 |
| WO | WO 98/36784 | 8/1998 |
| WO | WO 99/07308 | 2/1999 |
| WO | WO 01/14387 | 3/2001 |
| WO | WO 01/45763 | 6/2001 |
| WO | WO 02/26162 | 4/2002 |
| WO | WO 02/26281 | 4/2002 |
| WO | WO 02/32347 | 4/2002 |
| WO | WO 02/056790 | 7/2002 |
| WO | WO 03/022807 | 3/2003 |
| WO | WO 03/026718 | 4/2003 |
| WO | WO 03/090684 | 11/2003 |
| WO | WO 03/090818 | 11/2003 |
| WO | WO 2004/043292 | 5/2004 |
| WO | WO 2006/020742 | 2/2006 |

OTHER PUBLICATIONS

Lombardo et al. "ElogPoct: a tool for lipophilicity determination in drug discovery," J. Med. Chem, vol. 43, 2000, pp. 2922-2928.
European Search Report dated Oct. 14, 2009, filed in related European Patent Application No. 09011015.
Denny, W.A. and Cain, B.F., "Potential antitumor agents. 27. Quantitative structure—antileukemic (L 1210) activity relationships for the omega-[4-(9-acridinylamino)phenyl]alkanoic acids", *Journal of Medicinal Chemistry*, 21(5): 2190-2200 (1990).

Dibra, A. et al., "Influence of Stent Surface Topography on the Outcomes of Patents Undergoing Coronary Stenting: A Randomized Double-Blind Controlled Trial", *Catherization and Cardiovascular Interventions*, 65:374-380 (2005).

Ichihashi, T. et al., "A quantitative concept of the mechanism of intestinal lymphatic transfer of lipophilic molecules", *Pharmaceutical Research*, 11(4):508-512 (1994).

Schwartz et al., "Restenosis After Balloon Angioplasty—A Practical Proliferative Model in Porcine Coronary Arteries", *Circulation*, 84(6):2190-2200 (1990).

Su, SoH. et al., "Expandable Bioresorbable Endovascular Stent. I. Fabrication and Properties", Annals of Biomedical Engineering, 31:667-677 (2003).

DRUG-DELIVERY ENDOVASCULAR STENT AND METHOD FOR TREATING RESTENOSIS

This application claims the benefit of U.S. Provisional Application No. 60/613,071 filed Sep. 24, 2004, which is incorporated herewith by reference in its entirety.

BACKGROUND

A stent is a type of endovascular implant, usually generally tubular in shape, typically having a lattice, connected-wire tubular construction which is expandable to be permanently inserted into a blood vessel to provide mechanical support to the vessel and to maintain or re-establish a flow channel during or following angioplasty. The support structure of the stent is designed to prevent early collapse of a vessel that has been weakened and damaged by angioplasty. Insertion of stents has been shown to prevent negative remodeling and spasm of the vessel while healing of the damaged vessel wall proceeds over a period of months.

During the healing process, inflammation caused by angioplasty and stent implant injury often causes smooth muscle cell proliferation and regrowth inside the stent, thus partially closing the flow channel, and thereby reducing or eliminating the beneficial effect of the angioplasty/stenting procedure. This process is called restenosis. Blood clots may also form inside of the newly implanted stent due to the thrombotic nature of the stent surfaces, even when biocompatible materials are used to form the stent.

While large blood clots may not form during the angioplasty procedure itself or immediately post-procedure due to the current practice of injecting powerful anti-platelet drugs into the blood circulation, some thrombosis is always present, at least on a microscopic level, on stent surfaces and it is thought to play a significant role in the early stages of restenosis by establishing a biocompatible matrix on the surfaces of the stent whereupon smooth muscle cells may subsequently attach and multiply (Farb et al., *Circulation*, 110(8): 940-947, 2004).

Stent coatings are known which contain bioactive agents that are designed to reduce or eliminate thrombosis or restenosis. Such bioactive agents may be dispersed or dissolved in either a bio-durable or bio-erodable polymer matrix which is applied as a coating over the entire filament surface. After implantation, the bioactive agent diffuses out of the polymer matrix and preferably into the surrounding tissue.

If the polymer is bioerodable, in addition to release of the drug through the process of diffusion, the bioactive agent may also be released as the polymer degrades or dissolves, making the agent more readily available to the surrounding tissue environment. Bioerodable stents and biodurable stents are known where the outer surfaces or even the entire bulk of the polymer material is porous. For example, PCT Publication No. WO 99/07308, which is commonly owned with the present application, discloses such stents, and is expressly incorporated by reference herein. When bioerodable polymers are used as drug delivery coatings, porosity is variously claimed to aid tissue ingrowth, make the erosion of the polymer more predictable, or to regulate or enhance the rate of drug release, as, for example, disclosed in U.S. Pat. Nos. 6,099,562, 5,873,904, 5,342,348, 5,873,904, 5,707,385, 5,824,048, 5,527,337, 5,306,286, and 6,013,853.

A variety of agents specifically claimed to inhibit smooth muscle-cell proliferation, and thus inhibit restenosis, have been proposed for release from endovascular stents. As examples, U.S. Pat. No. 6,159,488 describes the use of a quinazolinone derivative; U.S. Pat. No. 6,171,609, the use of taxol, and U.S. Pat. No. 6,258,121, the use of paclitaxel, a cytotoxic agent thought to be the active ingredient in the agent taxol. The metal silver is cited in U.S. Pat. No. 5,873,904. Tranilast, a membrane stabilizing agent thought to have anti-inflammatory properties is disclosed in U.S. Pat. No. 5,733,327. More recently, rapamycin, an immunosuppressant reported to suppress both smooth muscle cell and endothelial cell growth, has been shown to have improved effectiveness against restenosis when delivered from a polymer coating on a stent. See, for example, U.S. Pat. Nos. 5,288,711 and 6,153,252. Also, in PCT Publication No. WO 97/35575, the macrocyclic triene immunosuppressive compound everolimus and related compounds have been proposed for treating restenosis. Commonly owned PCT publications WO 2003/090684 A3 and WO 03/090818 describe a polymer composition containing a macrocyclic triene compound and an endovascular stent and method for treating restenosis, respectively, both of which are incorporated herein by reference.

Given the advantages of implanting a stent designed to release a restenosis-inhibiting drug into vascular tissue following angioplasty, it would be desirable to produce a drug-eluting stent having additional advantages of (i) reducing the profile of the stent, both before and after placement at the site of vascular injury, (ii) eliminating chemical components that may cause irritation or inflammation at the stent site, and (iii) provide greater control of drug-release rate once the stent is placed at the site.

SUMMARY

In one aspect, the invention includes a radially expandable, endovascular stent designed for placement at a site of vascular injury, for inhibiting restenosis at the site. The invention includes a radially expandable body formed of one or more metallic filaments defining an outer surface, and attached to or formed in the outer surface, a liquid-infusible mechanical anchoring layer having an average thickness of at least 3 μm, and a drug coating composed of a substantially polymer-free composition of an anti-restenosis drug.

This drug coating has a substratum infused in the anchoring layer, for retaining the coating on the stent body when the stent is radially expanded at the site of vascular injury, and a substantially continuous surface stratum of drug that is brought into direct contact with the vessel walls at the site by such radial expansion. The rate of release of the anti-restenosis drug from the surface stratum into the vascular site is determined solely by the composition of the drug coating. The surface stratum of the drug has a preferred thickness of between about 5 and 30 μm, and preferably constitutes at least about 75 weight percent of the drug coating.

In one embodiment, the drug composition contains at least 90% by weight of an antirestenosis macrocyclic triene immunosuppressive compound having the structure:

where (i) R is H, a linear or branched short-chain alkyl, alkyl alcohol, alkyl ether or aldal group containing no more than ten carbon atoms. In exemplary compounds, R is $CH_2$—X—OH, and X is a linear or branched alkyl group containing 1 to 10 carbon atoms or $(CH_2)_n$—O—$(CH_2)_n$, where n is 1-3.

In another aspect, the invention includes an improvement in a radially expandable stent intended for reducing the risk of restenosis at a vascular site of injury, by release of a macrocyclic triene immunosuppressive compound from an intact drug-containing coating formed on an outer, vessel-contacting surface of a stent body. Drug release from the coating to the tissues lining the vascular site is direct, i.e., not limited by any diffusion-limiting membrane between the coating and vessel.

The intact drug-containing coating in the improvement is (i) composed of a substantially polymer-free composition of a macrocyclic triene immunosuppressive compound having the structure:

where (i) R is H, a linear or branched short-chain alkyl, alkyl alcohol, alkyl ether or aldal group containing no more than ten carbon atoms.

In exemplary compounds, R is $CH_2$—X—OH, and X is a linear or branched alkyl group containing 1 to 10 carbon atoms or $(CH_2)_n$—O—$(CH_2)_n$, where n is 1-3.

The improved stent may have a radially expandable body formed of one or more metallic filaments defining an outer surface, and attached to the outer surface, a liquid-infusible mechanical anchoring layer having an average thickness of at least 3 μm.

In still another aspect, the invention provides a method for achieving an effective rate of release of an anti-restenosis drug from a radially expandable stent placed within a vessel at a vascular site of injury. The method includes bringing the vessel in contact with a substantially continuous, substantially polymer-free surface drug coating containing at least about 90 weight percent of an anti-restenosis drug, where the rate of release of the anti-restenosis drug from the coating is determined solely by the composition of the drug coating. In a preferred embodiment, the drug has the structure:

where (i) R is H, a linear or branched short-chain alkyl, alkyl alcohol, alkyl ether or aldal group containing no more than ten carbon atoms. In exemplary compounds, R is $CH_2$—X—OH, and X is a linear or branched alkyl group containing 1 to 10 carbon atoms or $(CH_2)_n$—O—$(CH_2)_n$, where n is 1-3.

Also disclosed is a method of producing a radially expandable, endovascular stent designed for placement at a site of vascular injury, for inhibiting restenosis at the site. The method includes applying a substantially polymer-free, liquid composition of an anti-restenosis drug to a radially expandable stent body formed of one or more metallic filaments defining an outer surface, and having attached thereto or formed therein, a liquid-infusible mechanical anchoring layer having an average thickness of at least about 3 μm. The amount of liquid composition applied is sufficient to infuse the composition into said anchoring layer, to form a drug coating substratum within the layer, and to form over the substratum, a substantially continuous surface stratum of drug, wherein the rate of release of the anti-restenosis drug from the surface stratum into said site of vascular injury is determined solely by the composition of said drug coating.

These and other objects and features of the invention will become more fully apparent when the following detailed description of the invention is read in conjunction with the accompanying drawings.

DETAILED DESCRIPTION

I. Definitions

The following terms have the definitions given herein, unless indicated otherwise "Inhibiting restenosis" means reducing the extent of restenosis observed following a vascular "overstretch" injury, as measured by a reduction in average percentage of vascular stenosis at a selected time following stent placement, e.g., 1-6 months.

A "liquid-infusible mechanical anchoring layer" refers to stent surface features that provide interstices or vertically projecting surface features and/or regions of undercuts or recesses with substantially vertical walls into which a solution of drug can be drawn, e.g., by capillary forces. The thickness of such layer refers to the average thickness of the layer, e.g., average depth of the infusible portion of the layer.

A "substantially polymer-free drug composition" refers to a liquid or hardened drug layer in which polymer crosslinking makes virtually no contribution to the integrity of the composition in its hardened form. The term does not preclude the presence of soluble polymers, such as heparin, which make little or no contribution to the structure of the hardened drug layer, or polymers added to increase the viscosity of a liquid drug composition.

A "substantially continuous surface stratum" of a drug coating refers to a layer of drug composition that forms a substantially continuous expanse of drug composition undisturbed by irregular surface structures attached to or formed on the underlying metal stent.

The rate of release of an anti-restenosis drug from the surface stratum "is determined solely by the composition of the drug coating" where drug release kinetics, as determined—for example, by placing the coated stent in a selected drug-release environment—depends only on the solubility properties of the drug and any additives therein, e.g., lipid or other hydrophobic binder material in the surrounding tissue environment. This is in contrast to stents in which the rate of release of drug from an outer drug-release coating relies on (i) the presence of a cross-linked polymer matrix in which drug is embedded, (ii) the geometry of surface pores in which drug is carried or (iii) the presence of a porous, diffusion-limiting membrane covering the drug coating.

II. Endovascular Stent

Figure 1A:
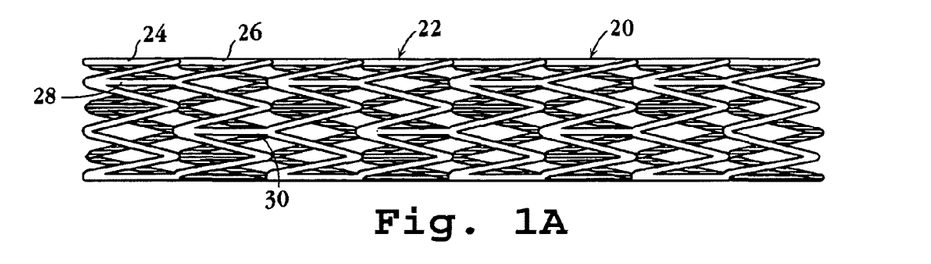
FIGS. 1A and 1B illustrate an endovascular stent having a metal-filament body and shown in contracted (FIG. 1A) and expanded (FIG. 1B) conditions.
Figure 1B:
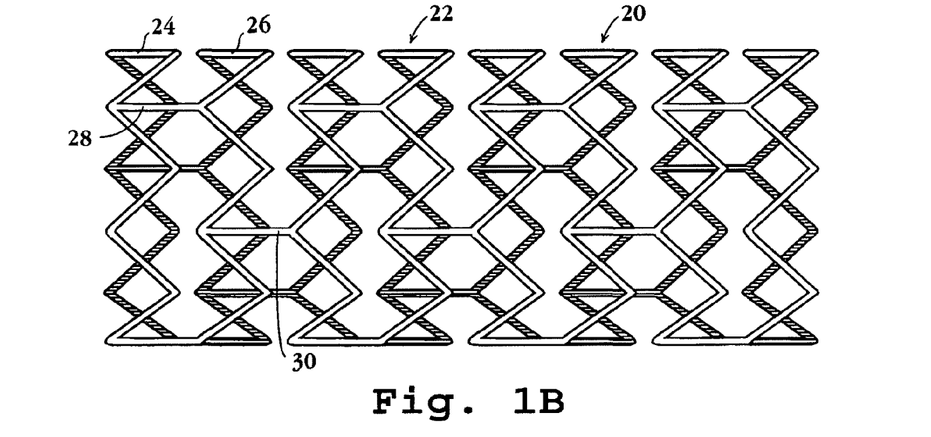

FIGS. 1A and 1B show a stent 20 constructed in accordance with the invention, in the stent's contracted and expanded states, respectively. The stent includes a structural member or body 22 and an outer coating for holding and releasing an anti-restenosis compound, as will be described further below with reference to FIGS. 3-5.

A. Stent Body

In the embodiment shown in FIGS. 1A and 1B, the stent body is formed of a plurality of linked tubular members by filaments, such as members 24, 26. Each member has an expandable zig-zag, sawtooth, or sinusoidal wave structure. At least some of the members are linked by axial links, such as links 28, 30 joining the peaks and troughs of adjacent members. As can be appreciated, this construction allows the stent to be expanded from a contracted condition, shown in FIG. 1A, to an expanded condition, shown in FIG. 1B, with little or no change in the length of the stent. It will be appreciated that the peaks and troughs of adjacent members may be offset, whereby at least some of the members are linked by axial links joining the trough of one member to the peak of the adjacent member. At the same time, the relatively infrequent links between peaks and troughs of adjacent tubular members allows the stent to accommodate bending. This feature may be particularly important when the stent is being delivered to a vascular site in its contracted state, in or on a catheter. It will be appreciated that any number of links between the adjacent members is contemplated. The stent has a typical contracted-state diameter (FIG. 1A) of between about 0.5-2 mm, more preferably about 0.71 to 1.65 mm, and a length of between about 5-100 mm. In its expanded state, shown in FIG. 1B, the stent diameter is at least twice and up to 8-9 times that of the stent in its contracted state. Thus, a stent with a contracted diameter of between about 0.7 to 1.5 mm may expand radially to a selected expanded state of between about 2-8 mm or more.

Stents having this general stent-body architecture of linked, expandable tubular members are known, for example, as described in PCT Publication No. WO 99/07308, which is commonly owned with the present application, and which is expressly incorporated by reference herein. Further examples are described in U.S. Pat. Nos. 6,190,406, 6,042,606, 5,860,999, 6,129,755, or 5,902,317, which patents are incorporated by reference herein. Alternatively, the structural member in the stent may have a continuous helical ribbon construction, that is, where the stent body is formed of a single continuous ribbon-like coil, and the ribbon forms the stent filaments. The basic requirement of the stent body is that it be expandable, upon deployment at a vascular injury site, and that it is suitable for receiving a drug-containing coating on its outer surface, for delivering drug contained in the coating into the vessel wall (i.e. medial, adventitial, and endothelial layers of tissue) lining the vascular target site. Preferably, the body also has a lattice or open structure, allowing endothelial cell wall ingrowth "through" the stent from outside to inside. The special features of the stent body used in supporting a drug coating will be considered in the section below. The metal or metal alloy forming the stent may include cobalt-chromium alloys, stainless steel, and platinum-iridium alloys.

Figure 2:
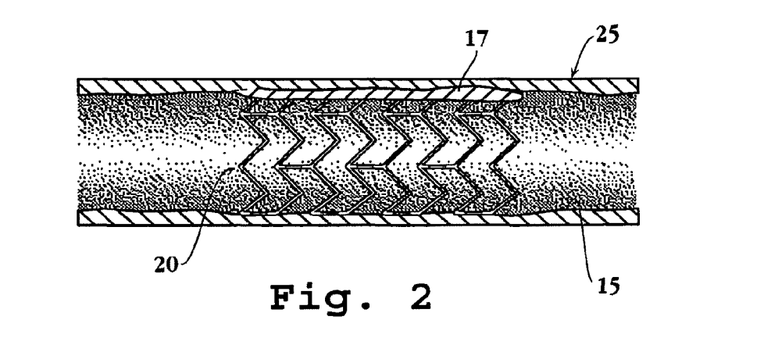
FIG. 2 shows a cross section of the stent of the invention placed at an intravascular site.

FIG. 2 shows the placement of the stent 20 at an intravascular site of injury in a vessel 25. The figure shows the stent in its expanded condition, after delivery to the site in a contracted condition, and radial expansion to an extent that presses the drug-coated stent-body filaments against the walls of the vessel 17. This placement anchors the stent within the vessel and brings the drug coating on the outer surface of the stent into direct contact with the tissues lining the vessel 15, for drug delivery directly from the drug coating to the cells lining the vessel.

B. Mechanical Anchoring Layer

Figure 3:
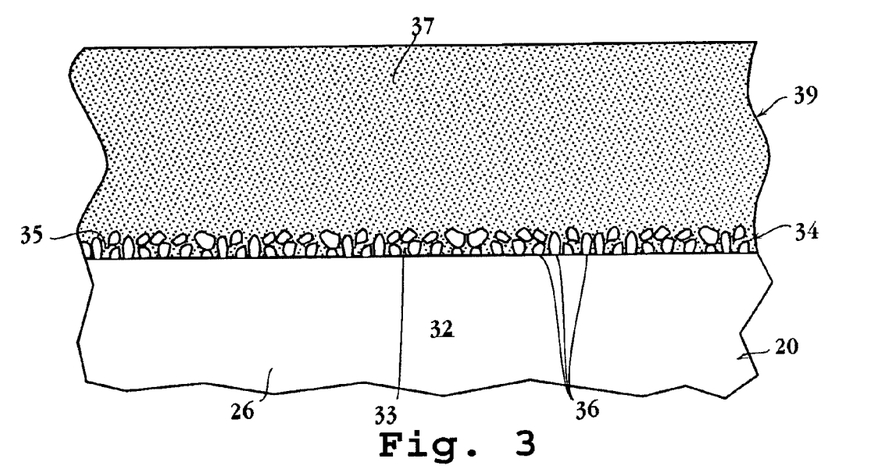
FIG. 3 is an enlarged cross-sectional portion of a stent-body filament, showing a mechanical anchoring layer on the filament and the drug coating and its two strata.

FIG. 3 shows, in enlarged view, a portion of a filament 26 in stent 20. The filament includes a filament body 32 having an upper or outer surface 33 which will face the vessel wall when the stent is operatively placed in a vessel. Formed on or attached to the upper surface of the filament is a liquid-infusible mechanical anchoring layer 34. In terms of its microstructure, layer 34 typically includes an array of projections or nodes, such as nodes 36. The anchoring layer is preferably formed on the outer, vessel-facing side of the stent-body filaments only, so that the drug layer carried on the stent is localized in this outwardly face side if the stent.

The stent (filament) body may be formed, for example, of cobalt/chromium, stainless steel, or platinum/iridium. The liquid-infusible mechanical anchoring layer may be composed of a similar of closely matched metal or alloy, for example, by electroplating the anchoring layer over the stent body.

Figure 4:
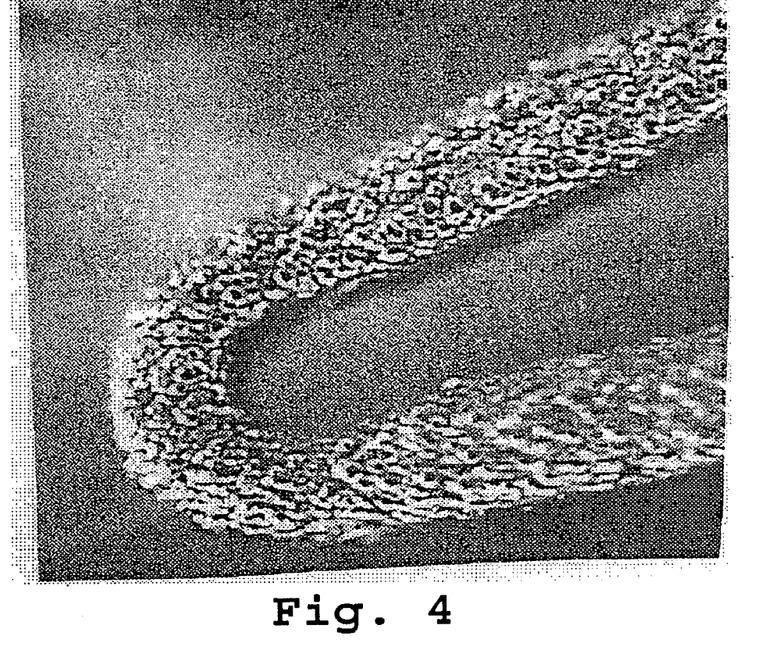
FIG. 4 is a photomicrograph of a portion of a filament in a stent formed in accordance with the invention.
Figure 5:
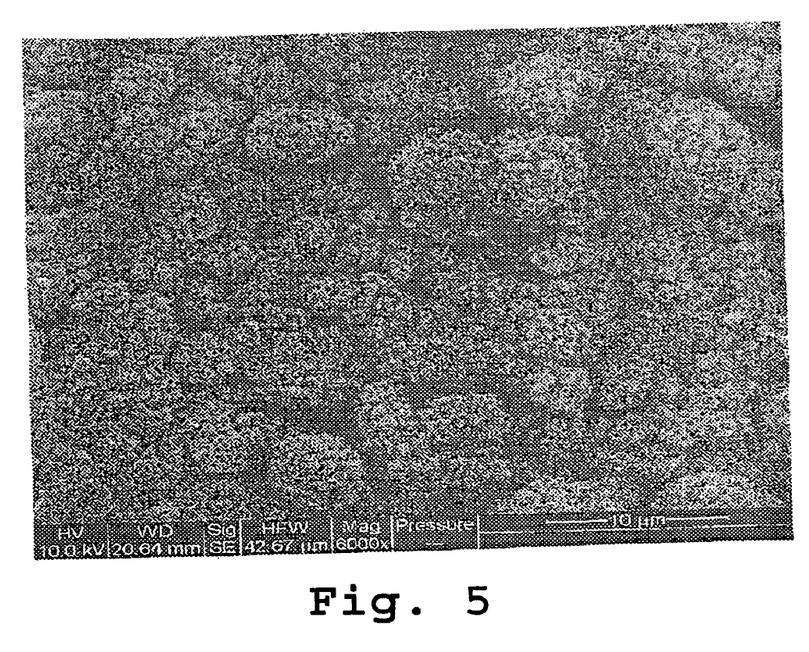
FIG. 5 is a scanning electron micrograph of the stent surface shown in FIG. 4.

FIG. 4 is a photomicrograph, at about 100× magnification, showing a portion of a stent filament having an exemplary mechanical anchoring layer formed on its outer (outwardly-facing) surface. As seen, the surface is highly irregular, providing an infusible surface layer formed of clusters of irregular shaped surface nodes or projections. As seen best in FIG. 5, these surface projections, which are cauliflower-like in appearance, have average sizes in the 2-8 micron size range, undercut surfaces, and form interstices among the array of projections that allow for infusion of drug solution into the layer, e.g., by capillarity. The thickness of the layer, as measured as an average thickness from the stent body, is preferably at least 3 microns, typically about 3-10 microns. The interstices among and between the projections are irregular and may extend through several adjacent projections. The void volume of the infusible surface layer is preferably between about 10-50%, more typically, about 20-40% of the total volume of the layer.

The mechanical anchoring layer described above is preferably formed by an electroplating method in which the stent and a source of the metal plating, e.g., a platinum bar, serve as the two electrodes of the system. In conventional electroplating methods, the current applied across the two electrodes is relatively low, allowing the plate to form in an even and controlled way, thus forming a smooth surface with a polished, mirror-like surface. However, as the electroplating current is increased, the plate build up becomes more irregular, leading to irregular-size and shaped projections such as those seen in FIG. 5.

Methods for electroplating to achieve a desired thickness and surface structure are known to those in the art. In one exemplary method, a platinum stent (cathode) and platinum bar (anode) were used as the electrodes in a conventional plating apparatus, using a platinum AP RTU from Technic, Inc. (Anaheim, Calif.) as the bath with the resulting anchoring layer shown in FIGS. 4-5. The temperature of the bath was adjusted to 160° F. and an applied voltage of 2.5 volts the total plating time was 15 minutes. It will be appreciated that at least one of the bath temperature, voltage, and total plating time may be adjusted to achieve the desired thickness and structure for the anchoring layer.

It will be appreciated that a variety mechanical anchoring layers with a variety of microstructures and formed in a variety of ways will be suitable for the present invention. It is only necessary that the anchoring layer have a microstructure capable of anchoring a drug layer on the stent so that the layer remains intact when the stent is expanded from its contracted to expanded state during stent placement. Other types of anchoring layers and their method of formation are discussed below.

One type of anchoring layer has a series of irregularly-shaped projections or reticulated microstructure, formed by microplating, e.g., a gold microplate, under high-current conditions. The electroplating layer may result in layers or stacks of irregular-shaped particles, e.g., in the 1-5 micron size range, forming a particle sieve like that resembling packed sand in its ability to take up a liquid applied to the surface. A reticulated surface may also be formed by vapor depositing or sputtering a surface coat onto the stent filaments, under rapid deposition conditions that leads to the build up of surface nodules.

In another embodiment, a surface containing recesses is formed by etching the stent's outer surface to form irregular voids. The voids are preferably interconnected, forming interstices within the anchoring layer. This type of surface layer illustrates one formed in the outer surface region of the stent body, rather than formed on the stent surface by deposition of addition of material to the surface. Methods for producing irregular etching of a metal surface are known. Alternatively, photolithographic methods of forming microstructure, such as described in U.S. Pat. Nos. 6,274,294 and 6,019,784 may be employed.

In still another approach, small particles, e.g., sintered particles in the 1-5 micron size range, may be applied to the stent surface, and affixed thereto with sintering or the like. In this approach, the particles may be applied with suitable adhesive that can be removed by pyrolysis during the sintering process. The layer may be built up by successive applications of particles.

C. Drug-Coating

With reference again to FIG. 3, the drug coating in the stent of the invention, indicated generally at 39, has a substratum 35 infused in the anchoring layer, for retaining the coating on the stent body when the stent is radially expanded at the site of vascular injury, and a substantially continuous surface stratum 37 of drug that is brought into direct contact with the vessel walls at stent placement. As can be appreciated from the section above, the substratum of the drug coating prefer- ably has dendritic projections within the stent's anchoring layer, to provide integral cohesion with the anchoring layer, but in any case is "interlocked" with the microstructure of the anchoring layer, e.g., because of filling regions of undercut in the anchoring layer within recesses or between surface nodules. This interlocking is important is preventing portions of the drug coating from separating and flaking off the stent during stent expansion.

The surface stratum 37 is integrally formed with the anchoring substratum, and forms a continuous expanse of drug, as shown, from which drug is released after stent placement. The surface stratum is typically about 5-30 microns or more in thickness, compared with the thickness of the anchoring substratum which is typically about 3-10 microns. The relative amounts of drug in the two strata is typically about 20:1 to 1:1, more typically about 10:1 to 4:1, where the substratum of the coating constitutes about 10-50% of the total drug coating, and preferably about 25% of less. Thus, the majority of drug release from the coating occurs from the continuous outer layer, where drug release kinetics is determined solely by the nature of the drug in the coating and, optionally, by additives in the coating that may alter the overall hydrophobic nature of the drug coating.

A variety of anti-restenosis compounds may be employed in invention, including anti-proliferative agents, such as taxol (paclitaxel), antisense compounds, doxorubicin, and most particularly, macrocyclic triene immunosuppressive compounds having the general structure indicated below, and also referred to generally as "limus" compounds. Some of the latter class of compounds, and their synthesis, are described, for example in U.S. Pat. Nos. 4,650,803, 5,288,711, 5,516, 781, 5,665,772 and 6,153,252, in PCT Publication No. WO 97/35575, in U.S. Pat. No. 6,273,913 B1, and in U.S. Patent Application Nos. 60/176,086, 2000/021217A1, and 2001/002935A1, all of which are incorporated herein by reference. An exemplary macrocyclic triene immunosuppressive compound has the form:

where (i) R is H, a linear or branched short-chain alkyl, alkyl alcohol, alkyl ether or aldal group containing no more than ten carbon atoms. In exemplary compounds, R is $CH_2$—X—OH, and X is a linear or branched alkyl group containing 1 to 10 carbon atoms or $(CH_2)_n$—O—$(CH_2)_n$, where n is 1-3, e.g., $(CH_2)_2$—O—$(CH_2)_2$ (also referred to herein as Biolimus A-9).

Another drug that is contemplated is pioglitazone, an oral anti-diabetic drug that acts primarily by decreasing insulin resistance. The compound inhibits growth factor-induced proliferation of smooth muscle cells in vitro and has been shown to reduce intimal hyperplasia after balloon angioplasty-induced vascular injury. The compound is slightly soluble in ethanol and acetone, and insoluble in water.

Another suitable compound is erythropoietin (EPO) a polypeptide involved in induction of red blood cells. EPO has been shown to stimulate endothelial progenitor cell mobilization in an animal model, and has also revealed protected effects in an infracted heart.

The coating may additionally include a second bioactive agent effective to minimize blood-related events, such as clotting, that may be stimulated by the original vascular injury, the presence of the stent; or to improve vascular healing at the injury site. Exemplary second agents include anti-platelet, fibrinolytic, or thrombolytic agents in soluble crystalline form. Exemplary anti-platelet, fibrinolytic, or thrombolytic agents are heparin, aspirin, hirudin, ticlopidine, eptifibatide, urokinase, streptokinase, tissue plasminogen activator (TPA), or mixtures thereof.

The coating may also include binders or small molecules designed to optimize the tissue solubility of the drug coating, to produce a desired cohesiveness in the drug coating, and a desired drug release rate in the implanted stent. In one aspect of solubility, the hydrophobicity of drugs is typically expressed as log P (log partition coefficient) between octanol and water, with a log P value>4 indicating a compound which will typically be strongly attracted (i.e. soluble) to lipophilic binding sites in tissues and poorly soluble in water and blood. Using a modified HPLC method for determining log P values (Lombardo et al., *J. Med Chem.*, 43:2922, 2000), studies conducted in support of the present invention have determined lop P values for a number of the above limus and other compounds. These range from 6.51 for rapamycin (R=H above), 6.70 for everolimus (R=$CH_2$—$CH_2$—OH, above), 7.63 for Biolimus A9 (R=$(CH_2)_2$—O—$(CH_2)_2$, above, and 4.68 for paclitaxel.

In general, it is desirable that the anti-restenosis compound have a relatively high log P value, e.g., greater than 4, to provide high solubility in tissues surrounding the stent, low solubility in water to prevent washout of the drug coating by blood, and integrity or cohesiveness to the drug coating, particularly for maintaining the structural integrity of the coating between the two strata in the coating following stent implant. Alternatively, the drug coating may be formulated to contain a hydrophobic molecule, e.g., a lipid molecule, such as lecithin, or other binder or carrier to provide cohesion and improved solubility in tissues. Conversely, where a compound is so hydrophobic that its release rate from the coating is too slow, the coating may be formulated with relatively hydrophilic molecules, e.g., short chain polyethylene glycol or the like to speed up the release rate of the drug.

Figure 7:
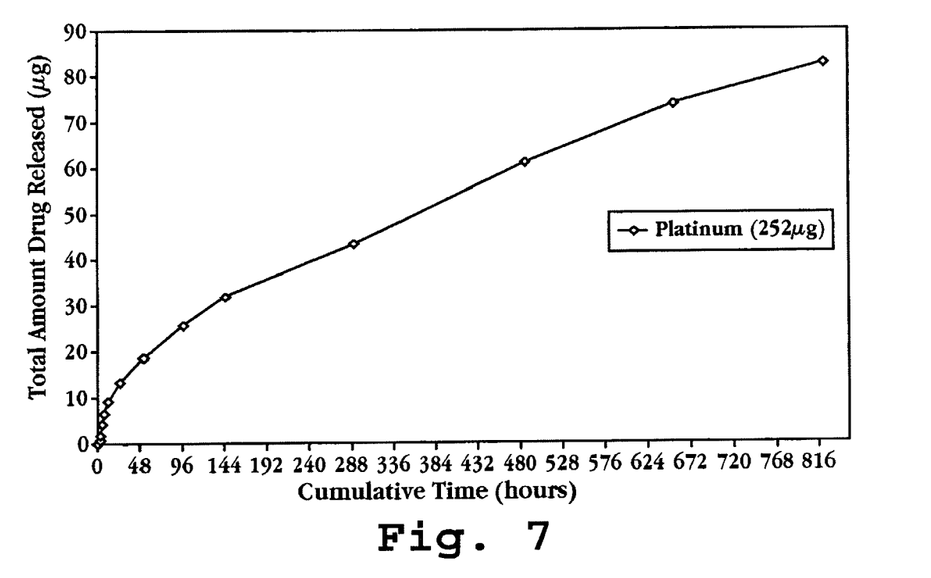
FIG. 7 is an elution profile in PBS of the drug Biolimus A-9 from the stent of the invention as measured by the total amount of drug released in μg over cumulative time in hours.

FIG. 7 shows a drug-release rate curve for Biolimus A-9 (252 μg) on a platinum-coated stent (platinum-plated anchoring layer) over a 34 day period. As seen, about one-third of the drug has eluted from the stent by day 34. It will be appreciated that the actual rate of drug release in vivo will be much greater, e.g., the bulk of the drug released will be released within the first few days following implantation, due to the greater hydrophobicity of the cell-membrane environment in vivo. However, the in vitro release in a purely aqueous medium provides a useful standard for formulating the drug coating, to achieve an effective drug release rate in vivo and also to achieve, a desired drug-layer cohesiveness.

A preferred coating includes at least about 90% by weight of the restenosis-inhibiting drug and up to 10% by weight additives, such as binders or agents to optimize release rate. Although the coating may contain solute polymer species, such as polyethylene glycol as a hydrophilic additive, heparin or EPO, the coating contains substantially no cross-linked polymer capable of providing structural support to the coating.

D. Stent Coating Methods

Figure 6:
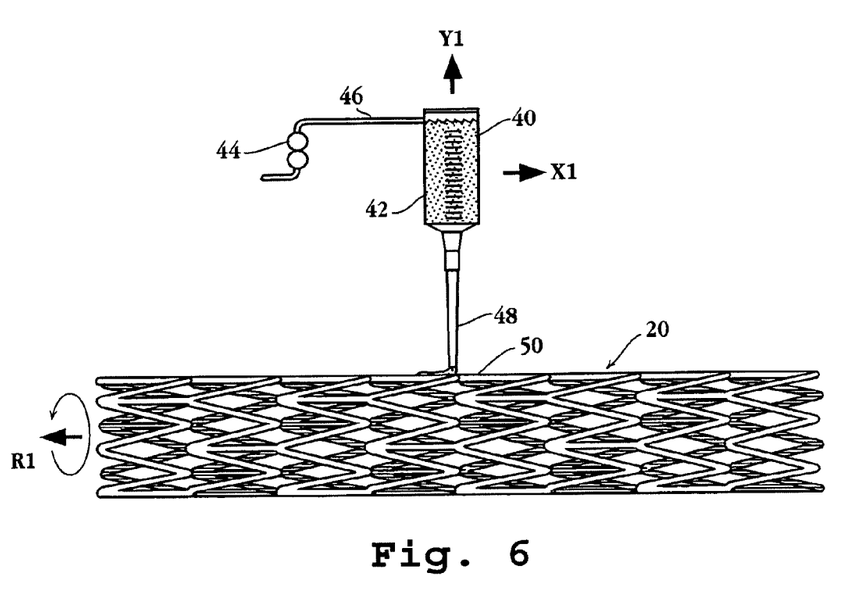
FIG. 6 illustrates a robotic delivery device for applying a drug layer to a stent.

FIG. 6 illustrates a robotic device useful in depositing the drug coating on the anchoring layer of the stent filaments 50. A drug solution or mixture 40 is made by dissolving the restenosis-inhibiting drug, and any other components of the coating, to a suitable solvent. One preferred solvent for the deposition of a hydrophobic compound such, as a limus compound, is ethyl acetate, at a drug concentration of between about 25-100 mg/ml, typically about 50 mg/ml. Other lower-alkyl acetates, such as methyl or propyl acetate are also suitable, as may be a number of other solvents capable of dissolving the compound at the concentrations indicated. Typically, the viscosity of the solvent mixture is prepared by varying the amount of solvent ranging from about 2 centipoise to about 2000 centipoise, and typically can be about 50 to 700 centipoise. If desired, polymer molecules may be added to increase solution viscosity.

The drug solution is placed in a pressurizable reservoir 42. Connected to the reservoir is a fluid pressurization pump 44. The pressurization pump may be any source of pressure capable of urging the solvent mixture to move at a programmed rate through a solution delivery tube 46. The pressure pump 44 is under the control of a microcontroller (not shown), as is well known in the field of precision dispensing systems. For example, such a microcontroller may comprise 4-Axis Dispensing Robot Model numbers I&J500-R and I&J750-R available from I&J Fisnar Inc. (Fair Lawn, N.J.), either of which are controllable through an RS-232C communications interface by a personal computer, or precision dispensing systems such as the Automove A-400 available from Asymtek (Carlsbad, Calif.). A suitable software program for controlling an RS232C interface may comprise the Fluidmove system, also available from Asymtek Inc. (Carlsbad, Calif.).

Attached to reservoir 42, for example, at the bottom of the reservoir, is a solution delivery tube 48 for delivery of the solvent mixture to the surface of the stent. The pressurizable reservoir 42 and delivery tube 48 are mounted to a moveable support (not shown) which is capable of moving the solvent delivery tube in small steps such as 0.2 mm per step, or continuously, along the longitudinal axis of the stent as is illustrated by arrow X1. The moveable support for pressurizable reservoir 42 and delivery tube 48 is also capable of moving the tip (distal end) of the delivery tube closer to the microfilament surface or up away from the microfilament surface in small steps as shown by arrow Y1.

The uncoated stent is gripped by a rotating chuck contacting the inner surface of the stent at least one end. In this manner, the stent may be rotated along the longitudinal axis as seen at R1. Axial rotation of the stent can be accomplished in small degree steps, such as 0.5 degree per step, to reposition the uppermost surface of the stent structure for coating by the delivery tube by attachment of a stepper motor to the chuck as is well known in the art. If desirable, the stent can be rotated continuously. The method of precisely positioning a low volume fluid delivery device is well known in the field of X-Y-Z solvent dispensing systems and can be incorporated into the present invention. Alternatively, the delivery tube can be held at a fixed position and, in addition to the rotation movement, the stent is moved along its longitudinal direction to accomplish the coating process.

The action of the fluid pressurizing pump, X1 and Y1 positioning of the fluid delivery tube, and R1 positioning of the stent are typically coordinated by a digital controller and computer software program, such that the precisely required amount of solution is deposited wherever desired on the surfaces of the stent, whereupon the solvent is allowed to escape.

The deposition may be carried out so that the thickness of the final drug layer varies over the length of the stent, e.g., the ends of the stent may have a thicker drug layer to reduce restenosis effects that may be localized to the ends of the stent. Similarly, the side regions of the stent ends may be coated to offset end effects.

Suitable X-Y-Z positioning tables and moveable supports are commercially available such as those available from I&J Fisnar Inc. (Fair Lawn, N.J.). The solution delivery tube preferred dimensions are preferably between 18-28 gauge stainless steel hypotubes mounted to a suitable locking connector. Such delivery tubes may be obtained from EFD Inc. (East Providence, R.I.). EFD publishes a selection guide for Special Purpose Tips. The preferred tips are number 5118-1/4-B through 5121-1/4-B "Burr-free passivated stainless steel tips with ¼" length for fast point-to-point dispensing of particle-filled or thick materials", number 51150VAL-B "Oval stainless steel tips apply thick pastes, sealants, and epoxies in flat ribbon deposits", and number 5121-TLC-B through 5125-TLC-B "Resists clogging of cyanoacrylates and provides additional deposit control for low viscosity fluids. Crimped and Teflon lined" all available from EFD Inc. (East Providence, R.I.). It will be appreciated that any number of commercially available tips are suitable for use with the robotic device. Any number of disposable pressurizable solution reservoirs are suitable and commercially available such as stock number 1000Y5148 through 1000Y 5152F available from EFD Inc. (East Providence, R.I.). An alternate tip for use with the invention is a glass micro-capillary with an I.D. of about 0.0005 to 0.002 inch, such as about 0.001 inch, which is available from VWR Catalog No. 15401-560 "Microhematocrit Tubes", 60 mm length, I.D. 0.5-0.6 mm. The tubes may further be drawn under a Bunsen burner to achieve the desired I.D. for precise application of the drug/solvent mixture. It will be appreciated that more than one of the fluid dispensing tube types may be used working in concert to form the coating, or alternately to use more than one moveable solution reservoir equipped with different tips, or containing different viscosity solutions or different chemical makeup of the multiple solutions in the same process to form the coating.

A suitable programmable microcontroller to operate the stepper motor, and XYZ table is available from Asymtek, Inc. A suitable chuck and stepper motor system is available from Edmund Scientific (Barrington, N.J.).

Typically, as described above, the coating is applied directly onto the outside support surface(s) of the stent in an amount, when dried, to produce a drug-layer of the desired thickness. As the drug solution is applied, a portion will infuse into the mechanical anchoring layer, and the remainder will form a beaded ribbon along the top surface of the filament. To complete the formation of the coating, the coating layer is dried under vacuum, e.g., at 20 inches Hg, until it forms a hardened, solvent-free layer. Ideally, the coating should have a glassine appearance at this stage, indicating a desired coating integrity. A coating that does not have a glassine appearance, or appears to be powdery in appearance, is likely to be unsuitable, and indicates that the drug should be applied in another solvent or in combination with additives that enhanced the cohesiveness of the coating.

An alternative method of applying the coating to the stent, if there is sufficient capillary attraction of the coating to the stent surface, may be to dip all or part of the stent into a reservoir of the drug solution, whereupon the drug is drawn up into the interstices of the coating. Further, the stent may be sprayed with the drug solution, whereupon the drug is drawn into the interstices of the coating.

III. Methods of Use and Performance Characteristics

This section describes vascular treatment methods in accordance with the invention, and the performance characteristics of stents constructed in accordance with the invention.

The methods of the invention are designed to minimize the risk and/or extent of restenosis in a patient who has received localized vascular injury, or who is at risk of vascular occlusion. Typically the vascular injury is produced during an angiographic procedure to open a partially occluded vessel, such as a coronary or peripheral vascular artery. In the angiographic procedure, a balloon catheter is placed at the occlusion site, and a distal-end balloon is inflated and deflated one or more times to force the occluded vessel open. This vessel expansion, particularly involving surface trauma at the vessel wall where plaque may be dislodged, often produces enough localized injury that the vessel responds over time by inflammation, cell proliferation leading to positive remodeling, and reocclusion. Not surprisingly, the occurrence or severity of this process, known as restenosis, is often related to the extent of vessel stretching and injury produced by the angiographic procedure. Particularly where overstretching is 35% or more, restenosis occurs with high frequency and often with substantial severity, i.e., vascular occlusion.

In practicing the present invention, the stent is placed in its contracted state typically at the distal end of a catheter, either within the catheter lumen, or in a contracted state on a distal end balloon. The distal catheter end is then guided to the injury site, or the site of potential occlusion, and released from the catheter, e.g., by using a trip wire to release the stent into the site, if the stent is self-expanding, or by expanding the stent on a balloon by balloon inflation, until the stent contacts the vessel walls, in effect, implanting the stent into the tissue wall at the site. Once deployed at the site, the stent immediately begins to release active compound into the cells lining the vascular site, to inhibit cellular proliferation.

Trials in a swine restenosis animal model as generally described by Schwartz et al. ("Restenosis After Balloon Angioplasty—A Practical Proliferative Model in Porcine Coronary Arteries", *Circulation,* 82:(6) 2190-2200, 1990.) demonstrate the ability of the stent of this invention to reduce the extent of restenosis. Briefly, studies conducted in support of the present invention compared the extent of restenosis at 28 days following stent implantation, in metal stents having an electroplated platinum anchoring layer, with or without a drug coating of Biolimus A-9. The presence of drug significantly reduced the extent of restenosis observed at the end of the 28-day study.

From the foregoing, it can be seen how various objects and features of the invention are met. The stent has a reduced profile, for a given amount of anti-restenosis drug on the stent, by virtue of the absence of polymer-sleeve material used as a reservoir for drug on the surface of the stent. This allows greater vessel opening, and thus improved blood flow, with less vessel stretching.

Polymeric stent coatings are known to produce increased vessel wall inflammation and restenosis, and the absence of polymeric components reduces inflammation and irritation at the vessel site, which can be caused, for example, by inflammatory cell reaction to breakdown of a biodegradable polymer or foreign body response to a stable polymer. At the same time, the drug coating of the current invention allows for greater control of drug release, and more constant release rate over time, since drug release kinetics are not dependent on diffusion through a polymer matrix, or across a porous outer layer, or from a porous metal matrix in the stent, but rely simply on dissolution of drug from the essentially pure-drug coating into the in the vascular environment. It is not until the drug coating is reduced down to the anchoring layer that drug release kinetics may be influenced in a minor way by another factor—in this case, the porosity of the mechanical anchoring layer.

Although the invention has been described with respect to particular embodiments and applications, it will be appreciated that various changes and modifications may be made without departing from the invention.

What is claimed is:

1. A method for achieving an effective rate of release of an anti-restenosis drug from a radially expandable stent placed within a vessel at a vascular site of injury, comprising bringing the vessel in contact with the stent having a substantially continuous, substantially polymer-free surface drug coating containing at least about 90 weight percent of an anti-restenosis drug, wherein the surface drug coating is attached to the stent using a liquid-infusible mechanical anchoring layer having an average thickness of at least 3 μm, where the surface drug coating is infused into the anchoring layer, forming a drug coating substratum within the anchoring layer, forming over the drug coating substratum, a substantially continuous surface stratum of drug and, wherein the rate of release of the anti-restenosis drug from the surface drug coating is determined solely by the composition of the surface drug coating, wherein the drug coating substratum constitutes no more than about 25% of said surface drug coating, and the anti-restenosis drug has the structure:

where (i) R is H, a linear or branched short-chain alkyl, alkyl alcohol, alkyl ether or aldal group containing no more than ten carbon atoms.

2. The method of claim 1, wherein is R is $CH_2$—X—OH, and X is a linear or branched alkyl group containing 1 to 10 carbon atoms or $(CH_2)_n$—O—$(CH_2)_n$, where n is 1-3.

3. The method of claim 2, wherein R is $(CH_2)_n$—O—$(CH_2)_n$ where n is 1-3.

4. The method of claim 1 wherein the surface stratum of drug has a thickness of between about 10 and 30 μm.

5. The method of claim 1, wherein said stent is formed of an alloy selected from the group consisting of cobalt/chromium, stainless steel, and platinum iridium.

6. The method of claim 1, wherein said liquid-infusible mechanical anchoring layer is produced by electroplating said layer over the stent.

* * * * *